United States Patent [19]

Drach et al.

[11] 4,064,163

[45] Dec. 20, 1977

[54] PROCESS FOR THE MANUFACTURE OF ALIPHATIC PHOSPHONIC ACIDS

[75] Inventors: John E. Drach, Cheltenham; Barry J. Pendell, Lansdale, both of Pa.

[73] Assignee: Amchem Products, Inc.

[21] Appl. No.: 755,927

[22] Filed: Dec. 30, 1976

[51] Int. Cl.² .............................................. C07F 9/38
[52] U.S. Cl. ............................................. 260/502.4 R
[58] Field of Search ................................. 260/502.4 R

[56] References Cited

U.S. PATENT DOCUMENTS

| | | | |
|---|---|---|---|
| 3,626,037 | 12/1971 | Randall et al. | 260/502.4 R |
| 3,808,265 | 4/1974 | Randall et al. | 260/502.4 R |
| 4,018,819 | 4/1977 | Rehn et al. | 260/502.4 R |

FOREIGN PATENT DOCUMENTS 1,565,742   3/1969   France .......................... 260/502.4 R

OTHER PUBLICATIONS

Gefter et al., "Chem. Abstracts", vol. 56 (1962), col. 501(g).

*Primary Examiner*—Joseph E. Evans
*Attorney, Agent, or Firm*—Robert C. Brown

[57] ABSTRACT

An improved process for the manufacture of an aliphatic phosphonic acid, particularly 2-chloroethylphosphonic acid, of the type wherein a diester of the aliphatic phosphonic acid, particularly bis-(2-chloroethyl)-2-chloroethylphosphonate, is reacted with anhydrous hydrogen halide, particularly hydrogen chloride, to produce a reaction product containing the aliphatic phosphonic acid, and the corresponding aliphatic halides particularly ethylene dichloride.

35 Claims, 1 Drawing Figure

CONCENTRATION VS. DISTANCE

RADIAL DISTANCE FROM
CENTER OF BUBBLE

PROCESS FOR THE MANUFACTURE OF ALIPHATIC PHOSPHONIC ACIDS

BACKGROUND OF THE INVENTION

This invention relates to a process for the manufacture of aliphatic phosphonic acids, and more particularly to a process for the manufacture of a 2-haloethylphosphonic acid and still more particularly, to the manufacture of 2-chloroethylphosphonic acid.

It is known in the art, that certain aliphatic phosphonic acids, particularly 2-haloethylphosphonic acids and derivatives thereof, are valuable as plant growth regulators in the agricultural field. The chloro compound, i.e. 2-chloroethylphosphonic acid has been used extensively as a plant growth regulator for increasing crop yield of, for example, pineapples, soybeans, and the like. The usefulness of these compounds is illustrated for example in the publication of Nature, vol. 218, page 974 (1969) by Cooke and Randall; and U.S. Pat. No. b 3,879,188, issued Apr. 22, 1975, entitled "Growth Regulation Process" invented by Fritz, Evans, and Cooke and assigned to the assignee of this application.

Processes for the manufacture of aliphatic phosphonic acids, more particularly, 2-chloroethylphosphonic acid have been described, for example in a. U.S. Pat. No. 3,787,486;
b. U.S. Pat. No. 3,808,265;
c. U.S. Pat. No. 3,888,953;
d. British Pat. No. 1,187,002;
e. British Pat. No. 1,229,593;
f. British Pat. No. 1,356,688;
g. British Pat. No. 1,373,513;
h. in certain relevant articles by Kabachnik, particularly Gefter and Kabachnik, Plasticeskie Massy, 1961, No. 1, pages 63–64; and
i. Chem. Abstracts, 1962, vol. 56, col. 501(g).

All of the foregoing references are incorporated herein by reference.

Generally, the following three-step process is described in these references:

PROCESS STEP I (a)   (b)   (c)

PROCESS STEP II (c)

(d)

PROCESS STEP III (d)

-continued (e)

Generally, one of the most critical steps in the process is PROCESS STEP III, the cleavage of the diester (d) with hydrogen chloride.

PROCESS STEP I, can, for example, be carried out as described in U.S. Pat. No. 3,888,953. This patent describes a process for the manufacture of tris(2-chloroethyl)phosphite (c) by simultaneously adding ethylene oxide (b) and phosphorus trichloride (a), in a molar ratio of between about 3.2:1 and about 3.9:1, to preformed tris(2-chloroethyl)phosphite (c) at a temperature between 0° C and about 10° C.

PROCESS STEP II, can for example, be carried out as described in British Pat. No. 1,229,593. This patent describes a process which involves heating to a temperature of between 140° C and 160° C a tris(2-chloroethyl)phosphite (c) in the presence of an organic solvent inert to the reaction to produce a bis(2-chloroethyl)2-chloroethylphosphonate (d).

As indicated previously, the critical step in the manufacture of aliphatic phosphonic acids, and more particularly 2-chloroethylphosphonic acid, is PROCESS STEP III, the cleavage of the diester (d) with a hydrogen halide.

One process for the manufacture of 2-haloethylphosphonic acid and derivatives thereof, is the cleavage of the corresponding diester with aqueous HCl. The aqueous HCl acid cleavage is a process well known in the art, and is illustrated, for example, in the text book of Kosolapoff, entitled "Organophosphorus Compounds", John Wiley & Sons, Inc., New York, around 1950, page 139. This reference indicates that esters of phosphonic acids are cleaved by hot hydrochloric and hydrobromic acid at atmospheric pressure.

U.S. Pat. No. 3,787,486 also describes a process for the manufacture of 2-chloroethylphosphonic acid which comprises treating bis(2-chloroethyl)-2-chloroethylphosphonate (d) under autogenous pressure and a temperature of about 100° C to 145° C with aqueous hydrochloric acid of about 20% to 45% strength to produce 2-chloroethylphosphonic acid. It is therefore well known in the art to use aqueous hydrochloric acid for cleaving the diester and to use aqueous hydrochloric acid under pressure.

Another process for the manufacture of 2-haloethylphosphonic acid and derivatives thereof, is the cleavage of the diester with anhydrous HCl at 100° C to 160° C. Anhydrous HCl acid cleavage is also well known in the art, as described, for example, by Gefter and Kabachnik, Plasticeskie, Massy, 1961, No. 1, pages 63–64.

British Pat. No. 1,187,002 describes a process for producing 2-haloethylphosphonic acid by introducing anhydrous HCl or HBR from an outside source into the diester which is stable at a temperature of above 140° C and heating the reaction mixture to a temperature of 140° C to 165° C for a period of time.

British Pat. No. 1,356,688 describes the manufacture of 2-chloroethylphosphonic acid by cleaving the diester with gaseous hydrogen chloride, with the exclusion of water, under elevated pressure at a temperature in the range of 100° C to 200° C.

Thus, the manufacture of 2-haloethylphosphonic acid by the cleavage of the corresponding diester with anhydrous HCl at atmospheric pressure and at elevated pressures is well known in the art.

Variations on the above processes for the manufacture of 2-haloethylphosphonic acid by cleavage of the diester are also well known in the art.

For example, British Pat. No. 1,373,513 describes a process for the manufacture of 2-chloroethylphosphonic acid which comprises cleaving the diester (d) with aqueous hydrochloric acid, optionally in the presence of gaseous hyrogen chloride, at a temperature of about 100° C and under an elevated pressure, continuously or discontinuously distilling off the 1,2-dichloroethane formed during the reaction and maintaining an elevated pressure by adding gaseous hydrogen chloride continuously or discontinuously during the reaction.

Another variation on the process of cleaving the diester is described in U.S. Pat. No. 3,808,265 which describes a process for the manufacture of 2-chloroethylphosphonic acid by reacting the diester (d) and concentrated aqueous hydrochloric acid under pressure of injected hydrogen chloride gas sufficient to replenish the reacted HCl and maintain the concentration of the aqueous hydrochloric acid above about 23% at a temperature of about 100° C to 145° C, cooling the reaction product to obtain a two phase liquid system consisting of an aqueous phase containing 2-chloroethylphosphonic acid and an organic phase containing ethylene dichloride, drawing off the ethylene dichloride phase and recovering 2-chloroethylphosphonic acid from the aqueous phase.

All of the above processes related to PROCESS STEP II involve the acid cleavage of the ester groups from the diester of the phosphonic acid to yield the corresponding phosphonic acid.

FORMULA A

This cleavage reaction for the manufacture of phosphonic acid occurs in a stepwise manner. The diester is converted to the half ester which, in turn, is cleaved to the phosphonic acid.

FORMULA B

This reaction is an example of a consecutive reaction.

For example, cleavage of the bis(2-chloroethyl)-2-chloroethyl phosphonate (the diester), by known prior art methods utilizing anhydrous HCl, depending upon reaction conditions and concentrations can produce from 45 to 84% 2-chloroethylphosphonic acid and from 3 to 30% of the mono-2-chloroethyl-2-chloroethyl phosphonate (the half ester).

A major impurity in the manufacture of 2-haloethylphosphonic acid, is the half ester of the corresponding acid.

It is highly desirable when applying 2-haloethylphosphonic acid, to plants, that the compositions applied be sufficiently free of impurities such as half esters of 2-haloethylphosphonic acids, to avoid the toxic, or potentially toxic effects of these impurities on plants. It is, thus, highly desirable to either remove the half ester from the crude reaction mixture obtained from the cleavage of the diester of the corresponding acid or to obtain, within reasonable operating parameters i.e. time, pressures, concentrations, etc. substantially complete reaction of the diester and half ester to 2-chloroethylphosphonic acid.

Generally, attempts have been made to purify 2-haloethylphosphonic acid manufactured from the prior art processes.

U.S. Pat. No. 3,626,037 describes the extraction with benzene of the mono ester of 2-chloroethylphosphonic acid from a reaction mixture containing the mono ester and 2-chloroethylphosphonic acid. The disadvantages of using benzene as a commercially practical extracting solvent are that it is highly flammable, acutely toxic to humans and gives poor phase separation when used as an extracting solvent for the half ester of haloethylphosphonic acid.

British Pat. No. 1,187,002 describes the extraction of the mono ester of 2-haloethylphosphonic acid from the crude reaction mixture with a halo-hydrocarbon of from 1 to 8 carbon atoms, such as chlorobenzene, dichlorobenzene, chloroform, tetrachloroethylene and preferably methylene chloride or ethylene dichloride. The disadvantages of using halo-hydrocarbons as commercially practical extracting solvents are that they are highly toxic to humans and a poor extracting solvent for the purification of 2-haloethylphosphonic acid.

The assignee attempted to solve the problem of manufacturing pure 2-haloethylphosphonic acid by extracting the half ester from an aqueous crude reaction mixture of the aliphatic phosphonic acid and the half ester by using an alkyl ester of carbonic acid, preferably diethylcarbonate, as an extracting solvent. The alkyl ester of carbonic acid may be recovered for re-use in the process. This process is described in U.S. Pat. No. 3,896,163.

A further attempt by the assignee to solve the problem of manufacturing pure 2-haloethylphosphonic acid, resulted in a process for separating an aliphatic phosphonic acid from an aliphatic phosphonic acid half ester, by extracting the half ester from an aqueous mixture, containing sodium sulfate, the aliphatic phosphonic acid and the half ester by using a halo-substituted alkyl of from 1 to 8 carbon atoms as an extracting solvent.

One serious drawback with attempting to obtain the highly pure aliphatic phosphonic acids necessary for commercial use by the addition of an extracting process to the process of manufacturing is that this extracting process involves an additional step with its concomitant increase in cost both in capital and operating expenses.

An object of this invention is to provide a novel process for manufacturing aliphatic phosphonic acids.

Another object of this invention is to provide a process for manufacturing highly pure aliphatic phosphonic acids at a low cost.

Still another object of this invention is to provide a novel manufacturing process which is particularly suitable for manufacturing 2-haloethylphosphonic acids, and more particularly 2-chloroethylphosphonic acid.

Still another object of this invention is to provide a novel process which is particularly suitable for manufacturing 2-haloethylphosphonic acids of highly pure nature under economically reasonable process parameters.

These and other objects of this invention will be more apparent from reading the following detailed description thereof.

DESCRIPTION OF INVENTION

Attainment of the above objects are made possible by the present invention, which includes a process for the manufacture of an aliphatic phosphonic acid, particularly 2-chloroethylphosphonic acid, of the type wherein a diester of the aliphatic phosphonic acid, particularly bis-(2-chloroethyl)-2-chloroethylphosphonate, is reacted with anhydrous hydrogen halide, particularly hydrogen chloride, to produce a reaction product containing the aliphatic phosphonic acid, and the corresponding aliphatic halides, particularly ethylene dichloride.

More particularly, this invention is a process for the manufacture of an aliphatic phosphonic acid of the formula:

of the type wherein a diester of the aliphatic phosphonic acid of the general formula:

is reacted with anhydrous hydrogen halide selected from the group consisting of hydrogen chloride, hydrogen bromide, hydrogen iodide and hydrogen fluoride to produce a reaction product containing the corresponding aliphatic phosphonic acid and the corresponding aliphatic halides, wherein $R_1$, $R_2$ and $R_3$ are each independently selected from the group consisting of substituted and unsubstituted aryl and alkyl, alkenyl, halo-substituted alkyl and halo-substituted alkenyl, having from 1 to 6 carbon atoms, wherein the improvement comprises
  a. reacting the diester and the anhydrous hydrogen halide at a first temperature of at least 100° C, at a low pressure and for a first period of time to form a first reaction product;
  b. subsequently reacting the first reaction product and the anhydrous hydrogen halide at a second temperature of at least 100° C, at a high pressure, said high pressure higher than said low pressure, for a second period of time to form a second reaction product; and
  c. removing the aliphatic halides from at least one reaction product.

Preferably, $R_1$, $R_2$ and $R_3$ are the same substituents. It is more preferable, that $R_1$, $R_2$ and $R_3$ are the halo-substituted alkyl substituents, particularly 2-chloroethyl substituents.

This process particularly relates to a process for the manufacture of 2-chloroethylphosphonic acid utilizing the diester bis-(2-chloroethyl)-2-chloroethylphosphonate and wherein the anhydrous hydrogen halide is anhydrous hydrogen chloride.

As used herein the term "alkyl" represents straight or branched chain saturated hydrocarbons.

The term "alkenyl" represents straight or branched chain aliphatic hydrocarbons containing at least one double bond.

The terms "halo-substituted alkyl" and "halo-substituted alkenyl" include alkyl and alkenyl groups having one or more hydrogens replaced by a halogen which can be bonded to the same or different carbon atoms in the alkyl or alkenyl group.

The term "halo", as used herein, includes all four halogens, namely chlorine, bromine, iodine and fluorine.

The term "aryl", as used herein, includes both mono- and polycyclic aryl substituents, such as phenyl, naphthyl and other condensed ring systems.

As only representative examples of the phosphonic acids, or mixtures thereof, which may be produced by the process of this invention, there may be mentioned the following:
  1. vinyl phosphonic acid,
  2. 1-chloroethylphosphonic acid,
  3. 2-chloroethylphosphonic acid,
  4. 1-chloropropylphosphonic acid,
  5. 2-chloropropylphosphonic acid,
  6. 2-chlorobutylphosphonic acid,
  7. methylphosphonic acid,
  8. ethylphosphonic acid,
  9. propylphosphonic acid, and
  10. butylphosphonic acid.

As indicated previously this process is particularly designed for the manufacture of 2-chloroethylphosphonic acid, a valuable plant growth regulator used in the agricultural field, however, this invention contemplates a process for the manufacture of any of the aliphatic phosphonic acids encompassed by the general formula above and the use of any of the diesters of the aliphatic phosphonic acid encompassed by the general formula above.

The preferred aliphatic phosphonic acid, 2-chloroethylphosphonic acid, is manufactured by utilizing the diester, bis-(2-chloroethyl)-2-chloroethylphosphonate and, preferably, anhydrous hydrogen chloride. The aliphatic halide produced by this reaction is ethylene dichloride.

However, as noted above 2-chloroethylphosphonic acid may also be manufactured by any of the other anhydrous hydrogen halides. Another preferred anhydrous hydrogen halide is anhydrous hydrogen bromide.

Further, this invention envisions the manufacture of 2-chloroethylphosphonic acid from other diesters, wherein $R_1$ is the 2-chloroethyl substituent.

The step of (a) reacting the diester and the anhydrous hydrogen halide and the step of (b) subsequently reacting the first reaction product and the anhydrous hydrogen halide are both accomplished at at least 100° C. Preferably, the first and second temperatures are both from about 140° C to about 160° C. The temperatures should not exceed 200° C. Below 100° C the reaction kinetics are such as to cause the reaction to proceed too slowly, whereas above 200° C product and raw material decomposition interferes with the reactions.

One of the critical aspects of this invention is carrying out the step of (a) reacting the diester and the anhydrous hydrogen halide at a "low pressure", and the step of (b)

subsequently reacting the first reaction product and the anhydrous hydrogen halide at "high pressure", wherein the "high pressure" is higher than said "low pressure".

By the use of the term "high pressure" and "low pressure" this invention contemplates practically any "low pressure" and any "high pressure" as long as the "high pressure" is higher than the "low pressure". The effect of this on the reaction rate and economics is to produce an aliphatic phosphonic acid more economically, in a shorter period of time and of a higher purity than processes which utilize a constant low pressure for the same period of time. Further, there is no significant advantage to utilizing a constant high pressure for the same period of time, and in fact a constant high pressure is possibly detrimental to reaction rates and is economically disadvantageous.

Preferably, for economic reasons, the low pressure should be at least 14 psia and the high pressure, at least 20 psia. Preferably, the low pressure is from about 14 psia to about 30 psia and the high pressure is from 30 psia to about 50 psia.

By the use of the term "psia" it is meant pounds per square inch of pressure as an absolute value. For example, 14.7 psia (atmospheric pressure) is equivalent to 0 psig., i.e. pounds per square inch gauge.

Preferably, as indicated previously, the high pressure is from about 30 psia to about 50 psia, however, this invention contemplates the use of any "high pressure" during the second period of time. The kinetics of the reaction is such that the higher pressure is during the second period of time, the more rapidly the reaction proceeds. The only limitation on the high pressure utilized is equipment limitations and the economics of the process.

The preferred low pressure, as indicated previously is from about 14 psia to about 30 psia, the only limitation therein is also equipment limitations and the economics of the process. Surprisingly, tests indicate that the lower the pressure during the first period of time the more rapidly the process will proceed. For economic reasons, the most preferable low pressure is atmospheric pressure.

The process step of reacting the diester and the anhydrous hydrogen halide is accomplished in "a first period of time" to form a first reaction product and then subsequently, the step of reacting the first reaction product and the anhydrous hydrogen halide is accomplished in a "second period of time" to form a second reaction product.

The length of time for the "first period of time", generally is a period of time such that the total process reaction rate can benefit from the application of the high pressure during the second period of time. The first period of time is related to the particular aliphatic phosphonic acid to be manufactured, the particular diester used in the maufacture of the aliphatic acid and the particular anhydrous hydrogen halide utilized in the manufacturing process.

The "second period of time", generally, is the period of time necessary to produce the aliphatic phosphonic acid of the required concentration, i.e. purity. For example, in the preferred process for the manufacture of 2-chloroethylphosphonic acid by reacting bis-(2-chloroethyl)-2-chloroethylphosphonate with anhydrous hydrogen chloride it is preferred that the first period of time is until the first reaction product contains at least 70% by weight of 2-chloroethylphosphonic acid. After this period of time an increase in pressure to the high pressure will have a beneficial effect on the total process reaction rate. The first period of time in the preferred process for the manufacture of 2-chloroethylphosphonic acid is usually, at least about 25 hours and preferably from about 25 to about 35 hours.

Further, the second period of time in the preferred process for the manufacture of 2-chloroethylphosphonic acid is until the second reaction product contains a required concentration of at least about 80% by weight of 2-chloroethylphosphonic acid. The second period of time in the preferred process for the manufacture of 2-chloroethylphosphonic acid is at least about 10 hours. Preferably however, the reaction time is from about 10 hours to about 16 hours. Commercially acceptable 2-chloroethylphosphonic acid for most agricultural uses is generally considered to have a minimum concentration of 85% by weight of 2-chloroethylphosphonic acid in the second reaction product. This can usually be accomplished within a second period of time of about 13 hours.

It has further been discovered that the step of removing the aliphatic halides should be accomplished in a continuous manner. This invention contemplates the removal of the aliphatic halides from at least one reaction product, however it is preferred to continuously remove the aliphatic halides from both the first and second reaction product.

In the preferred process of manufacture of 2-chloroethylphosphonic acid the aliphatic halide is ethylene dichloride. In this process the ethylene dichloride is removed continuously from both the first and second reaction products. Preferably, this step of removing ethylene dichloride is accomplished simultaneously with the steps of (a) reacting the diester and the anhydrous hydrogen chloride and (b) reacting the first reaction product and the anhydrous hydrogen chloride. This is accomplished by (i) introducing continuously into the first and second reaction products an entrance stream comprised of anhydrous hydrogen chloride; and (ii) removing continuously from the first and second reaction products an exit stream comprised of unreacted anhydrous hydrogen chloride and ethylene dichloride.

It has been discovered that the reaction kinetics are such that the exit stream flowrate during the first period of time should be greater than the exit stream flowrate during the second period of time. However, increased reaction rates may be obtained in the total process as long as the aliphatic halide i.e. ethylene dichloride, is removed from at least one reaction product.

It has been discovered that the weight ratio of the exit stream flowrate during the first period of time to the exit stream flowrate during the second period of time should be about (3 to 6) : 1. This particular ratio of exit stream flowrates optimizes the total process.

For economic reasons it is preferable that the unreacted anhydrous hydrogen halide i.e. hydrogen chloride, is separated from the exit stream and introduced into the entrance stream. For obvious reasons, it would be uneconomical and environmentally impractical to vent all the unreacted anhydrous hydrogen chloride the the atmosphere.

This invention is particularly concerned with a process for the manufacture of 2-chloroethylphosphonic acid of the type wherein bis-(2-chloroethyl)-2-phosphonate is reacted with anhydrous hydrogen chloride to produce a reaction product containing 2-chloroethylphosphonic acid and ethylene dichloride. The improvement that this invention contemplates in this type reaction is:

a. reacting bis-(2-chloroethyl)-2-chloroethyl phosphonate and anhydrous hydrogen chloride at a first temperature of at least 100° C, at a low pressure of at least about 14 psia for a first period of time to form a first reaction product, said first period of time is until the first reaction product contains at least about 70% by weight of 2-chloroethylphosphonic acid;

b. subsequently reacting the first reaction product and the anhydrous hydrogen chloride at a second temperature of at least 100° C, at a high pressure of at least about 30 psia, said high pressure higher than said low pressure, and for a second period of time to form a second reaction product, said second period of time is until the second reaction product contains a required concentration of at least about 80% by weight of 2-chloroethylphosphonic acid;

c. continuously removing ethylene dichloride from the first and second reaction products; and wherein the steps of (a) reacting bis-(2-chloroethylphosphonate and anhydrous hydrogen chloride, (b) reacting the first reaction product and anhydrous hydrogen chloride, and (c) removing ethylene dichloride are accomplished by:

i. introducing continuously into the first and second reaction products an entrance stream comprised of anhydrous hydrogen chloride;

ii. removing continuously from the first and second reaction products an exit stream comprised of unreacted anhydrous hydrogen chloride and ethylene dichloride.

In order that this invention may be more fully understood, it is convenient at this point to discuss some of the mechanisms thought to be involved in the process of manufacturing the aliphatic phosphonic acids, in particular, 2-chloroethylphosphonic acid. Of course, it is to be understood, that it is not intended that the invention should be bound to, or in any manner limited, by such theories.

The cleavage of the diester bis-(2-chloroethyl)-2-chloroethylphosphonate by the use of anhydrous hydrogen chloride to produce 2-chloroethylphosphonic acid falls into a class of reactions which is very complex.

In the most general case, the cleavage reaction is reversible. In the preferred process of reacting the anhydrous hydrogen chloride (HCl) with the bis-(2-chloroethyl)-2-chloroethyl phosphate (diester) and removing the ethylene dichloride (EDC) from the reaction product, the process can be visualized to occur in the following sequence of steps:

1. The hydrogen chloride gas diffuses from the bulk concentration in the bubble produced by introducing it into the liquid phase, i.e. the reaction product, through a film of stagnant gas to the bubble liquid interface;

2. The hydrogen chloride diffuses from the bubble liquid interface through a stagnant liquid film around the bubble to the bulk liquid phase. During this diffusion some of the hydrogen chloride reacts with the diester;

3. Mixing and diffusion of hydrogen chloride in the bulk liquid occur simultaneously with chemical reaction to form ethylene dichloride, the corresponding half ester and 2-chloroethylphosphonic acid;

4. Mixing and diffusion of the ethylene dichloride in the bulk liquid reaction product;

5. The ethylene dichloride diffuses from the bulk liquid phase reaction product through a stagnant liquid film around the bubble to the bubble liquid interface; and 6. The ethylene dichloride diffuses from the bubble liquid interface through a film of stagnant gas to the bulk concentration in the bubble, which passes through the liquid phase and is removed.

The process kinetics can be simplified by eliminating those steps which do not make a significant contribution to the overall resistance to mass transfer.

In general, diffusion in a gas phase occurs much more rapidly than diffusion in a liquid phase. At low gas densities, for example, the difference in relative rates is on the order of $10^4$. Therefore, Steps 1 and 6, above, are of little consequence in the overall reaction kinetics compared to Steps 2 and 5.

Also, in an agitated reactor, as is often the case in commercial reactors, the concentrations in the bulk liquid phase reaction product are nearly uniform. Therefore Step 4, above, and the mixing and diffusion part of Step 3, above, are also relatively unimportant.

Figure 1:
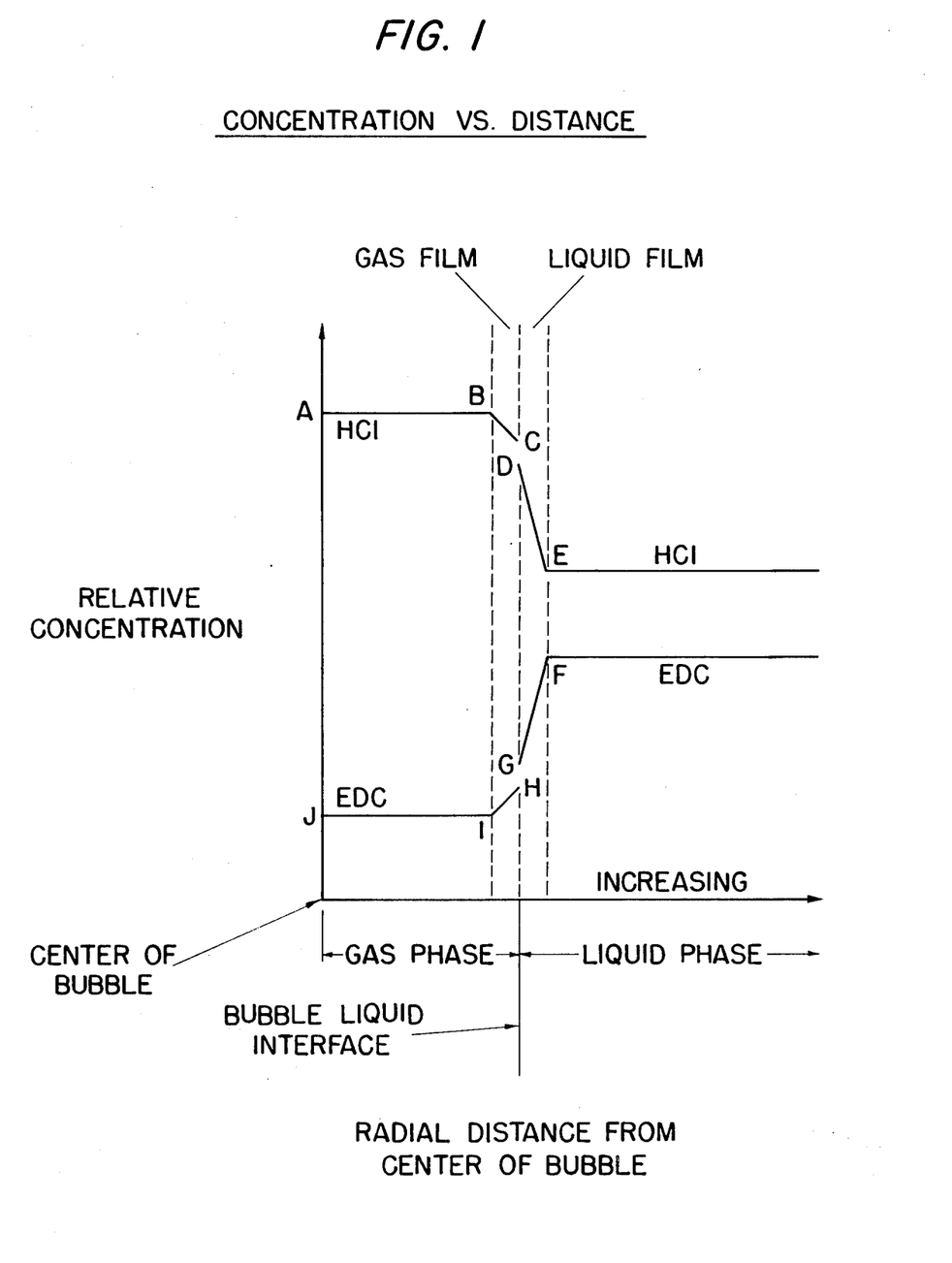

This simplified process is illustrated in FIG. 1.

The hydrogen chloride concentration is uniform throughout most of the bubble from Point A through Point B. The hydrogen chloride concentration drops slightly as it diffuses through the gas film starting at Point B to the bubble liquid interface at Point C. At the bubble liquid interface, the gas and liquid concentrations are in thermodynamic equilibrium, therefore, the hydrogen chloride concentration in the gas at Point C is in equilibrium with the hydrogen chloride concentration in the liquid at Point D. The hydrogen chloride concentration drops again as it diffuses through the liquid film from the bubble liquid interface at Point D to the bulk liquid concentration starting at Point E.

FIG. 1 shows a liner concentration gradient from Point D through Point E. This assumes that very little of the hydrogen chloride reacts in the liquid film. If this assumption were not true, Point D through E would probably be a curve with a steep slope at Point D and nearly flat at Point E.

The concentration of hydrogen chloride at Point E is that of the bulk liquid phase. In the bulk liquid phase, the hydrogen chloride reacts with the diester and the corresponding half ester to produce additional half ester, 2-chloroethylphosphonic acid, and ethylene dichloride according to the following reactions:

PROCESS STEP III-A $$ClC_2H_4-\overset{\overset{O}{\|}}{P}\overset{OC_2H_4Cl}{\underset{OC_2H_4Cl}{\diagdown}} + HCl \rightleftarrows ClC_2H_4-\overset{\overset{O}{\|}}{P}\overset{OC_2H_4Cl}{\underset{OH}{\diagdown}}$$

diester        half ester $$+ \; ClC_2H_4Cl$$

ethylene dichloride

PROCESS STEP III-B $$ClC_2H_4-\overset{\overset{O}{\|}}{P}\overset{OC_2H_4Cl}{\underset{OH}{\diagdown}} + HCl \rightleftarrows ClC_2H_4-\overset{\overset{O}{\|}}{P}\overset{OH}{\underset{OH}{\diagdown}}$$

half ester        2-chloroethyl-phosphonic acid

-continued $$+ ClC_2H_4Cl \text{ (ethylene dichloride)}$$

Likewise, the ethylene dichloride produced by the reaction diffuses from the bulk liquid concentration at Point F through the liquid film to the bubble liquid interface at Point G. The linear concentration gradient here also assumes that very little reaction occurs in the liquid film.

The ethylene dichloride concentration in the liquid at the interface, Point G, is in equilibrium with the ethylene dichloride concentration in the gas at the interface, Point H. The ethylene dichloride concentration then drops slightly as it diffuses through the fas film to Point I. The ethylene dichloride concentration at Point I is the same as that in most of the bubble.

In order to simplify the mathematical analysis, the gas phase resistance will be completely ignored. This assumes that the hydrogen chloride concentration at Point C is equal to the concentration at Point B and that the ethylene dichloride concentration at Point H is equal to the concentration at Point I.

According to Henry's law, the equilibrium relationship between a gas and a solvent is:

$$C = (\overline{P}/H)$$

wherein:
$\overline{P}$ = the partial pressure of the gas in the vapor base
$C$ = the concentration of the gas dissolved in the solvent, moles per unit volume.
$H$ = Henry's law constant for the particular system.

Therefore, at the bubble-liquid interface:
For hydrogen chloride (HCl):

$$C_{i_{HCl}} = (\overline{P}_{HCl}/H_{HCl})$$

For ethylene dichloride (EDC):

$$C_{i_{EDC}} = (\overline{P}_{EDC}/H_{EDC})$$

wherein:
$i$ = subscript indicating interface; and
$C_i$ = the concentration in the liquid at the bubble-liquid interface.

The rate of mass transfer from a high concentration to a low concentration may be expressed as $$r_m = k_l a_g (C_1 - C_2)$$

wherein:
l = subscript indicating liquid;
$k_l$ = the mass transfer coefficient for the particular system with units of length/time.
$a_g$ = gas-liquid interfacial surface area per unit volume of bubble-free liquid.
$C$ = the component concentration in the liquid with units of moles per unit volume.
$r_m$ = mass transfer rate units of moles per unit volume of bubble-free liquid.

Therefore, the rate of mass transfer into and out of the system is:
For hydrogen chloride:

$$r_{m_{HCl}} = k_{l_{HCl}} a_g (C_{i_{HCl}} - C_{l_{HCl}})$$

For ethylene dichloride:

$$r_{m_{EDC}} = k_{l_{EDC}} a_g (C_{l_{EDC}} - C_{i_{EDC}})$$

wherein:
$C_l$ = the component concentration in the bulk-liquid phase.

Substituting the bubble-liquid interfacial equilibrium expressions yields:
Equation (1) For hydrogen chloride:

$$r_{m_{HCl}} = k_{l_{HCl}} a_g (\overline{P}_{HCl}/H_{HCl} - C_{l_{HCl}})$$

Equation (2) For ethylene dichloride:

$$r_{m_{EDC}} = k_{l_{EDC}} a_g (C_{l_{EDC}} - \overline{P}_{EDC}/H_{EDC})$$

The exact nature of the kinetics of the reaction itself is not known, however. The reaction is consecutive with respect to the diester, half-ester, and 2-chloroethylphosphonic acid, and parallel with respect to hydrogen chloride and ethylene dichloride. During the course of the reaction, the diester concentration decreases, the half-ester concentration increases to a maximum and then decreases, and the 2-chloroethylphosphonic acid concentration increases.

The generalized mathematical relationship for the production of half-ester by PROCESS STEP III-A is:

Equation (3) $(r_{K_F})_A = (k_F)_A [HCl]^a [\text{diester}]^b$ wherein:
$F$ = subscript indicating forward reaction.
$k$ = intrinstic chemical rate constant.
$r_K$ = intrinsic chemical kinetic rate in units of moles per time per unit volume of bubble-free liquid.
[ ] = concentration in moles/volume of bubble-free liquid.

The generalized mathematical relationship for the reverse of PROCESS STEP III-A is:

Equation (4) $(r_{K_R})_A = (k_R)_A [EDC]^c [\text{half-ester}]^d$ wherein:
R = subscript indicating reverse reaction.
The corresponding expressions for PROCESS STEP III-B are:

Equation (5) $(r_{K_F})_B = (k_F)_B [HCl]^e [\text{half-ester}]^f$

Equation (6) $(r_{K_R})_B = (k_R)_B [EDC]^g [\text{2-chloroethylphosphonic acid}]^h$ The above analysis indicates that as pressure increases the rate of production of 2-chloroethylphosphonic acid increases, it does not indicate that a low pressure, followed by a high pressure will probably achieve a higher rate of production than a constant high pressure.

The above analysis further indicates that the removal of the ethylene dichloride from the reaction products is necessary for increasing the rate of production of 2-chloroethylphosphonic acid.

From the examples which follow, certain conclusions can be reached on the theoretical aspects of this invention.

Firstly, nearly all of the diester is consumed during the first 5 hours of reaction time. For this reason reaction PROCESS STEP III-B can be assumed to be essentially irreversible. Consequently it does not have a great effect on the overall reaction time. The limiting reaction rate is thus the conversion of the corresponding monoester to 2-chloroethylphosphonic acid. A mathematical relationship for this limiting chemical kinetic step is as follows:

$$r_k = K_F[HCl]^e[\text{half-ester}]^f - K_R[EDC]^g$$
[2-chloroethyl-*h*-phosphonic acid]

From the foregoing equation it can be seen that in order to increase the chemical kinetic rate ($r_K$), the value of $K_F$, the concentration of HCl and the concentration of the monoester should be maximized and the value of $K_R$, the concentration of EDC, and the concentration of 2-chloroethylphosphonic acid should be minimized.

In a commercial reaction there is very little that can be done about maximizing the concentration of the mono-ester and minimizing the concentation of 2-chloroethylphosphonic acid. However, the concentration of HCl can be maximized and the concentration of ethylene dichloride (EDC) can be minimized, as the process of this invention accomplishes.

During the process of this invention, a psuedo steady state is achieved, such that the rate of mass transfer of HCl into the liquid equals the rate of conversion of hydrogen chloride and mono-ester to 2-chloroethylphosphonic acid and ethylene dichloride which also equals the rate of mass transfer of the ethylene dichloride from liquid to gas. Therefore $$r_{m_{HCl}} = r_K = r_{m_{EDC}}$$

Pursuant to the previous equation, if the hydrogen chloride is being transferred into the liquid very quickly, maintaining a relatively high hydrogen chloride concentration and the ethylene dichloride is being transferred out of the liquid very quickly maintaining a relatively low ethylene dichloride concentration, the rate of conversion to 2-chloroethylphosphonic acid should decrease over a time interval. This is because the concentation of the monoester continually decreases causing $r_K$ to decrease. A graph of the conversion of 2-chloroethylphosphonic acid versus time would be logarithmic in such a situation. Under these conditions the overall reaction rate is said to be controlled by kinetics.

If, however, the rate of mass transfer of hydrogen chloride into the liquid is relatively slow, but the hydrogen chloride in the liquid reacts rapidly with the mono-ester to form 2-chloroethylphosphonic acid and ethylene dichloride, and the ethylene dichloride is transferred rapidly out of the liquid, then the reaction is controlled by the rate of mass transfer of hydrogen chloride. Equation (1) thus shows that the rate of reaction is essentially constant under these conditions and a graph of 2-chloroethylphosphonic acid concentration versus time would yield a straight line.

If, on the other hand, the rate of mass transfer of the ethylene dichloride out of the liquid is relatively slow, and the rate of hydrogen chloride mass transfer into the liquid and the reaction are relatively rapid, the overall reaction is controlled by the rate of mass transfer of ethylene dichloride. The ethylene dichloride concentration builds up until it slows down the reaction rate. Equation (2) thus shows that the rate of reaction is essentially constant under these conditions and a graph of 2-chloroethylphosphonic acid concentration versus time would yield a straight line.

The above generalizations assume that the properties of the reaction mixture do not vary too greatly. However, it is obvious that there are great changes in the reaction mixture which occur during the course of the reaction. Nevertheless, these generalizations do help to gain a qualitative understanding of the overall reaction mechanism.

An analysis of the following examples also indicates that during much of the reaction, mass transfer is controlling. The conversion rate during the first 5 hours is affected by initial rates. Early in the reaction there is very little hydrogen chloride or ethylene dichloride dissolved. At first the mass transfer of hydrogen chloride controls, then the reaction rate may become important and finally the rate of ethylene dichloride removal may become important. Consequently it is very difficult to analyze the reaction during the first five hours of time. After the conversion reaches at least 70% weight concentration of 2-chloroethylphosphonic acid in the reaction product, the intrinsic reaction rate becomes slow enough that it begins to retard the rate of conversion to 2-chloroethylphosphonic acid. Therefore, it appears that the order of magnitude of the intrinsic reaction rate and at least one of the mass transfer rates is the same.

An analysis of, for example, the reaction at 140° and 150° C and 0 psig at varying exit stream flowrates [Example 2] indicates that an increase in the exit stream flowrate increases the rate of conversion of 2-chloroethylphosphonic acid. If the reaction were controlling the intrinsic kinetic rate, exit stream flowrate would have no effect. As the exit stream flowrate is increased, the rate of mass transfer is increased and the overall reaction exit stream flowrate probably increases the amount of interfacial area, $a_g$. It would probably do this by increasing the mean residence time of the bubbles. In Equation (2) $a_g$ would increase for the same reason. In addition, $\overline{P}_{EDC}$ may be reduced. Therefore, either rate of mass transfer would be increased by an increase in exit stream flowrate.

An analysis of the Examples also indicates the effect of pressure at a constant exit stream flowrate, for example, at three pounds per hour and 150° C and 160° C, [Example 3]. An analysis shows that an increase in pressure surprisingly does not change and perhaps even somewhat decreases, the reaction rate during the mass transfer control period, i.e. first period of time.

In Equation (1), an increase in pressure from 0 psig to 30 psig would cause $a_g$ to decrease by a factor of 3 and $\overline{P}_{HCl}$ to increase by a factor of 3. Therefore, if the rate of HCl mass transfer were controlling, an increase in pressure should have very little effect on the overall reaction rate.

In Equation (2), an increase in pressure would decrease $a_g$ and increase $\overline{P}_{EDC}$. Both changes would decrease the rate of mass transfer of ethylene dichloride.

This indicates that the rate of ethylene dichloride mass transfer has a very definite influence on the overall rate of reaction.

In addition, Example 1, also indicates that the removal of ethylene dichloride is important. This Example demonstrates that the rate of reaction of HCl with 2-chloroethylphosphonic acid to form a mono-ester and ethylene dichloride is significant.

Other experiments performed in a similar manner to that of Example 1, also show that, with no exit stream flowrate, the rate of conversion to 2-chloroethylphosphonic acid virtually stops at a low level.

If the presence were released and the ethylene dichloride permitted to flash off of the reaction product and the system were repressurized the rate of conversion undergoes a similar incremental increase and then stops.

The following experiments also clearly indicate that the rate of mass transfer of ethylene dichloride plays a significant role in the overall reaction rate. However, the Examples do not eliminate the possibility that the rate of mass transfer of hydrogen chloride also contributes to the overall reaction rate. The intrinsic chemical kinetic rate appears to affect the overall rate only at higher conversions and at exit stream flowrates above 2 lbs/hr.

The following examples further show the effect of temperature on the overall reaction rate. The examples indicate that a higher temperature is favorable up to about 80% conversion i.e. during the first period of time. An increase in temperature during this period probably increases the intrinsic chemical kinetic rate as long as the ethylene dichloride concentration is kept low. In Equations (1) and (2), k would probably increase slightly and H would increase. This probably results in an overall decreasing effect on the rate of mass transfer of hydrogen chloride, but an increasing effect on the rate of mass transfer of ethylene dichloride.

If is difficult to determine whether the rate of mass transfer of ethylene dichloride or the intrinsic chemical rate is controlling. It may be that both are significant at 3 lbs./hr. exit stream flowrate. At the 1 and 2 lbs./hr. exit stream flowrate the Examples indicate that the ethylene dichloride mass transfer rate is controlling.

The following Examples further indicate that up to a conversion of at least 70%, and preferably 80% 2-chloroethylphosphonic acid in the reaction product, the reaction is controlled at least in part by the rate of ethylene dichloride mass transfer. A low pressure and high vent flowrate increase the the rate of ethylene dichloride mass transfer.

As the conversion approaches 70 to 80%, the reaction rate becomes increasingly more controlled by the intrinsic chemical kinetic rate. The amount of monoester present in the reaction product becomes small. In order to increase the intrinsic chemical rate, it is necessary to increase the concentration of hydrogen chloride in the liquid. This is accomplished by increasing the hydrogen chloride pressure. The rate of mass transfer of ethylene dichloride is less important at this point because very little ethylene dichloride is formed.

EXAMPLES

The following examples are illustrative of this invention and are not to be considered as limiting.

In all of the following Examples a reactor was charged with over 50 pounds of pure bis-(2-chloroethyl)-2-chloroethyl phosphonate and heated to the desired temperature by introducing steam into a jacket surrounding the reactor. The anhydrous hydrogen chloride gas was introduced into the reactor at the bottom of the reactor through a combination flush and diffuser valve. The exiting unreacted hydrogen chloride gas and the ethylene dichloride by product was removed from the reaction vessel and introduced into a condenser. The ethylene dichloride was condensed and removed from the exiting stream. The desired pressure and flowrate of gas exiting from th reaction were maintained by adjusting the anhydrous hydrogen chloride pressure entering the vessel.

The reaction time, the temperature of reaction, the pressure, the exit stream gas flowrate containing the unreacted hydrogen chloride and ethylene dichloride, and the weight percent concentration of 2-chloroethylphosphonic acid in the reaction product were monitored.

The weight percent concentrated of 2-chloroethylphosphonic acid in the reaction product was monitored and measured by methods well known in the art.

EXAMPLE I

COMPARATIVE EXAMPLE NO EXIT STREAM FLOWRATE

This Example indicates how the reaction proceeds when there is no step increase in pressure and no exit stream flowrate. In this Example, the pressure was maintained at 30 ± 2 psig (44.7 ± 2 psig). The reaction was run for 15 hours. Under these conditions, very low conversion rates resulted, and after 2 hours of reaction time, the conversion to 2-chloroethylphosphonic acid virtually stopped.

TABLE 1

COMPARATIVE EXAMPLE

| Period of Time (hours) | Reaction Temperature (° C) | Reaction Pressure (PSIG)[1] | Exit Stream Flowrate (lbs./hr.) | Weight % 2-chloroethyl-phosphonic acid in reaction product |
|---|---|---|---|---|
| 1 | 150 | 30 ± 2 | 0 | 13.8 |
| 2 | 150 | 30 ± 2 | 0 | 19.5 |
| 3 | 150 | 30 ± 2 | 0 | 19.6 |
| 4 | 150 | 30 ± 2 | 0 | 21.4 |
| 5 | 150 | 30 ± 2 | 0 | 21.5 |
| 10 | 150 | 30 ± 2 | 0 | 30.2 |
| 15 | 150 | 30 ± 2 | 0 | 22.7 |

[1]PSIG = pounds per square inch gauge.
PSIA = pounds per square inch absolute = 14.7 plus PSIG

EXAMPLE II

COMPARATIVE EXAMPLE

This Example shows the effect of removing continuously from the reaction products, an exit stream comprised of unreacted anhydrous hydrogen chloride and ethylene dichloride. An increase in the exit stream flowrate increases the rate of conversion to 2-chloroethylphosphonic acid. This Example indicates that if the reaction were controlled by the intrinsic kinetic rate, exit stream flowrate would have no effect on the percent conversion.

TABLE 2(a)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 140 | 0 | 2 | 32.8 |
| 10 | 140 | 0 | 2 | 42.2 |
| 15 | 140 | 0 | 2 | 51.2 |
| 20 | 140 | 0 | 2 | 59.5 |
| 25 | 140 | 0 | 2 | 63.4 |

TABLE 2(b)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 140 | 0 | 1 | 27.1 |
| 10 | 140 | 0 | 1 | 32.7 |
| 15 | 140 | 0 | 1 | 38.4 |
| 20 | 140 | 0 | 1 | 45.4 |
| 25 | 140 | 0 | 1 | 50.7 |

TABLE 2(c)
COMPARATIVE EXAMPLE
EFFECT OF VENT FLOWRATE AT 150° C AND 0 PSIG

| Experiment No. | | 1 | 2 | 3 | 4 |
|---|---|---|---|---|---|
| Temperature (° C) | | 150 | 150 | 150 | 150 |
| Pressure (PSIG) | | 0 | 0 | 0 | 0 |
| Exit Stream Flowrate (lbs./hr.) | | 0.5 | 1 | 2 | 3 |
| Weight % 2-chloroethyl-phosphonic acid in Reaction Product | | | | | |
| | 5 hrs. | 20.8% | 28.6% | 37.5% | 43.0% |
| | 10 hrs. | 27.8% | 35.6% | 49.0% | 58.3% |
| | 15 hrs. | 35.6% | 44.5% | 63.0% | 66.8% |
| | 20 hrs. | 39.4% | 51.9% | 70.8% | 74.9% |
| | 25 hrs. | 43.9% | 55.5% | 76.5% | 77.2% |
| | 30 hrs. | 55.1% | 63.8% | 79.4% | 80.4% |
| | 35 hrs. | | 68.2% | 80.4% | |

One sees from the above Example that as the exit stream flowrate is increased, the rate of conversion to 2-chloroethylphosphonic acid increases.

EXAMPLE III

COMPARATIVE EXAMPLES

This Example indicates the effect of pressure on conversion rate, at an exit stream flowrate of 3 lbs. per hour at 150° C and 160° C.

TABLE 3(a)
COMPARATIVE EXAMPLE
EFFECT OF PRESSURE AT 150° C AND 3 LBS./HR. EXIT STREAM FLOWRATE

| Experiment No. | | 1 | 2 | 3 |
|---|---|---|---|---|
| Temperature (° C) | | 150 | 150 | 150 |
| Pressure (PSIG) | | 0 | 15 ± 2 | 30 ± 2 |
| Exit Stream Flowrate (lbs./hr.) | | 3 | 3 | 3 |
| Weight % 2-chloroethyl-phosphonic acid in Reaction Product | | | | |
| | 5 hrs. | 43.0% | 37.3% | 37.6% |
| | 10 hrs. | 58.3% | 49.8% | 50.2% |
| | 15 hrs. | 66.8% | 61.4% | 56.8% |
| | 20 hrs. | 74.9% | 72.7% | 67.0% |
| | 25 hrs. | 77.2% | 79.6% | |
| | 30 hrs. | 80.4% | | |

TABLE 3(b)
COMPARATIVE EXAMPLE
EFFECT OF PRESSURE AT 160° C AND 3 LBS./HR. EXIT STREAM FLOWRATE

| Experiment No. | | 1 | 2 | 3 |
|---|---|---|---|---|
| Temperature (° C) | | 160 | 160 | 160 |
| Pressure (PSIG) | | 0 | 15 ± 2 | 30 ± 2 |
| Exit Stream Flowrate (lbs./hr.) | | 3 | 3 | 3 |
| Weight % 2-chloroethyl-phosphonic acid in Reaction Product | | | | |
| | 5 hrs. | 44.4% | 49.4% | 44.4% |
| | 10 hrs. | 60.4% | 62.1% | 52.0% |
| | 15 hrs. | 70.4% | 74.6% | 63.6% |
| | 20 hrs. | 76.1% | 81.7% | 68.9% |
| | 25 hrs. | 79.9% | 84.8% | 79.8% |
| | 30 hrs. | 82.0% | | |

The above Example clearly indicates that as pressure increases during the first 30 hours of reaction time i.e. the first period of time, that the rate of conversion to 2-chloroethylphosphonic acid remains about the same, or in fact may decrease somewhat.

EXAMPLE IV

COMPARATIVE EXAMPLE

This Example indicates the effect of temperature on the conversion rate to 2-chloroethylphosphonic acid during the first thirty hours of reaction time. From these tests it can be generalized that during the first 30 hours of reaction time i.e. the first period of time, the higher the temperature the greater the conversion rate. Subsequent to this period of time i.e. the second period of time, higher temperatures do not have an appreciable effect on conversion rate.

TABLE 4(a)
COMPARATIVE EXAMPLE
EFFECT OF TEMPERATURE AT 0 PSIG AND 1 LB./HR. EXIT STREAM FLOWRATE

| Experiment No. | | 1 | 2 | 3 |
|---|---|---|---|---|
| Temperature (° C) | | 140 | 150 | 160 |
| Pressure (PSIG) | | 0 | 0 | 0 |
| Exit Stream Flowrate (lbs./hr.) | | 1 | 1 | 1 |
| Weight % 2-chloroethyl-phosphonic acid in Reaction Product | | | | |
| | 5 hrs. | 27.1% | 28.6% | 30.4% |
| | 10 hrs. | 32.7% | 35.6% | 39.2% |
| | 15 hrs. | 38.4% | 44.5% | 49.4% |
| | 20 hrs. | 45.4% | 51.9% | 55.7% |
| | 25 hrs. | 50.7% | 55.5% | 59.6% |

TABLE 4(b)
COMPARATIVE EXAMPLE
EFFECT OF TEMPERATURE AT 0 PSIG AND 2 LBS./HR. EXIT STREAM FLOWRATE

| Experiment No. | | 1 | 2 | 3 |
|---|---|---|---|---|
| Temperature (° C) | | 140 | 150 | 160 |
| Pressure (PSIG) | | 0 | 0 | 0 |
| Exit Stream Flowrate (lbs./hr.) | | 2 | 2 | 2 |
| Weight % 2-chloroethyl-phosphonic acid in Reaction Product | | | | |
| | 5 hrs. | 32.8% | 37.5% | 30.8% |
| | 10 hrs. | 42.2% | 49.0% | 50.5% |
| | 15 hrs. | 51.2% | 63.0% | 55.5% |
| | 20 hrs. | 59.5% | 70.8% | 73.9% |
| | 25 hrs. | 63.4% | 76.5% | 77.8% |

TABLE 4(c)
COMPARATIVE EXAMPLE
EFFECT OF TEMPERATURE AT 0 PSIG AND 3 LBS./HR. EXIT STREAM FLOWRATE

| Experiment No. | | 1 | 2 | 3 |
|---|---|---|---|---|
| Temperature (° C) | | 140 | 150 | 160 |
| Pressure (PSIG) | | 0 | 0 | 0 |
| Exit Stream Flowrate (lbs./hr.) | | 3 | 3 | 3 |
| Weight % 2-chloroethyl-phosphonic acid in Reaction Product | | | | |
| | 5 hrs. | 34.5% | 37.8% | 44.4% |
| | 10 hrs. | 47.8% | 53.2% | 60.4% |
| | 15 hrs. | 56.3% | 64.4% | 70.4% |
| | 20 hrs. | 64.2% | 72.7% | 76.1% |
| | 25 hrs. | 68.4% | 77.0% | 79.9% |

TABLE 4(c)-continued
COMPARATIVE EXAMPLE
EFFECT OF TEMPERATURE AT 0 PSIG AND 3 LBS./HR. EXIT STREAM FLOWRATE

| | | | |
|---|---|---|---|
| 30 hrs. | 72.7% | 80.6% | 82.0% |
| 35 hrs. | 76.0% | | |

EXAMPLE V

This Example indicates the results of utilizing the process of this invention for the manufacture of 2-chloroethylphosphonic acid.

TABLE 5
EXPERIMENTS PERFORMED AT 150° C

| Experiment No. | | 1 | 2 | 3 | 4 | 5 |
|---|---|---|---|---|---|---|
| Diester Charge (lbs.) | | 59 | 56 | 55.5 | 58 | 59 |
| Weight % 2-chloroethyl- | 5 hrs. | 42.2% | 38.2% | 39.7% | 37.8% | 42.6% |
| phosphonic acid in | 10 hrs. | 52.5% | 57.3% | 54.3% | 53.2% | 53.7% |
| Reaction Product At | 15 hrs. | 65.6% | 67.0% | 65.4% | 64.4% | 64.4% |
| 0 PSIG at 3 lbs./hr. | 20 hrs. | 71.8% | 74.1% | 72.2% | 72.7% | 71.8% |
| Exit Stream Flowrate | 25 hrs. | 76.5% | 77.7% | 75.1% | 77.0% | 76.3% |
| | 30 hrs. | 79.6% | 80.1% | 79.3% | 80.6% | 80.2% |
| Weight % 2-chloroethyl- | 35 hrs. | 85.9% | | | | |
| phosphonic acid in | 40 hrs. | | | | | |
| Reaction Product At | 42 hrs. | 88.0% | | 89.0% | 87.8% | |
| 30 ± 2 PSIG and 1 | 43 hrs. | | 88.8% | | | 88.8% |
| lb./hr. Exit Stream | | | | | | |
| Flowrate | | | | | | |
| Total Reaction Product (lbs.) | | 27 | 25.5 | 25.5 | 28 | 27 |
| 2-chloroethylphosphonic acid manufactured (lbs. - 100%) | | 23.7 | 22.6 | 22.7 | 24.6 | 24.0 |

EXAMPLE VI

This Example indicates the use of the process of this invention at 140° C.

TABLE 6

| Period of Time (hours) | Reaction Temperature (° C) | Reaction Pressure (PSIG) | Exit Stream Flowrate (lbs./hr.) | Weight % 2-chloroethyl- phosphonic acid in reaction product |
|---|---|---|---|---|
| 5 | 140 | 0 | 3 | 34.5 |
| 10 | 140 | 0 | 3 | 47.8 |
| 15 | 140 | 0 | 3 | 56.3 |
| 20 | 140 | 0 | 3 | 64.2 |
| 25 | 140 | 0 | 3 | 68.4 |
| 30 | 140 | 0 | 3 | 72.7 |
| 35 | 140 | 0 | 3 | 76.0 |
| 43 | 140 | 30±2 | 0 | 81.3 |

EXAMPLE VII

This Example indicates the use of the process of this invention at 150° C.

TABLE 7(a)

| Period of Time (hours) | Reaction Temperature (° C) | Reaction Pressure (PSIG) | Exit Stream Flowrate (lbs./hr.) | Weight % 2-chloroethyl- phosphonic acid in reaction product |
|---|---|---|---|---|
| 5 | 150 | 0 | 2 | 37.5 |
| 10 | 150 | 0 | 2 | 49.0 |
| 15 | 150 | 0 | 2 | 63.0 |
| 20 | 150 | 0 | 2 | 70.8 |
| 25 | 150 | 0 | 2 | 76.5 |
| 30 | 150 | 0 | 2 | 79.4 |
| 35 | 150 | 0 | 2 | 80.4 |
| 41 | 150 | 15 – 20 | 0.5 | 85.5 |

TABLE 7(b)

| Period of Time (hours) | Reaction Temperature (° C) | Reaction Pressure (PSIG) | Exit Stream Flowrate (lbs./hr.) | Weight % 2-chloroethyl- phosphonic acid in reaction product |
|---|---|---|---|---|
| 5 | 150 | 0 | 3 | 43.0 |
| 10 | 150 | 0 | 3 | 58.3 |
| 15 | 150 | 0 | 3 | 66.8 |
| 20 | 150 | 0 | 3 | 74.9 |
| 25 | 150 | 0 | 3 | 77.2 |
| 30 | 150 | 0 | 3 | 80.4 |
| 35 | 150 | 15 – 20 | 0.5 | 84.8 |
| 41 | 150 | 15 – 20 | 0.5 | 87.0 |

TABLE 7(c)

| Period of Time (hours) | Reaction Temperature (° C) | Reaction Pressure (PSIG) | Exit Stream Flowrate (lbs./hr.) | Weight % 2-chloroethyl- phosphonic acid in reaction product |
|---|---|---|---|---|
| 5 | 150 | 0 | 3 | 42.5 |
| 10 | 150 | 0 | 3 | 56.8 |
| 15 | 150 | 0 | 3 | 67.7 |
| 20 | 150 | 0 | 3 | 74.2 |
| 25 | 150 | 0 | 3 | 77.7 |
| 30 | 150 | 0 | 3 | 81.5 |
| 35 | 150 | 30 ± 2 | 0 | 86.4 |
| 40 | 150 | 30 ± 2 | 0 | 87.2 |
| 45 | 150 | 30 ± 2 | 0 | 88.0 |
| 50 | 150 | 30 ± 2 | 2 – 3 | 89.3 |
| 55 | 150 | 30 ± 2 | 2 – 3 | 90.8 |
| 58 | 150 | 30 ± 2 | 2 – 3 | 90.3 |

TABLE 7(d)

| Period of Time (hours) | Reaction Temperature (° C) | Reaction Pressure (PSIG) | Exit Stream Flowrate (lbs./hr.) | Weight % 2-chloroethyl- phosphonic acid in reaction product |
|---|---|---|---|---|
| 5 | 150 | 0 | 3 | 42.6 |
| 10 | 150 | 0 | 3 | 53.7 |
| 15 | 150 | 0 | 3 | 64.4 |
| 20 | 150 | 0 | 3 | 71.8 |
| 25 | 150 | 0 | 3 | 76.3 |
| 30 | 150 | 0 | 3 | 80.2 |
| 43 | 150 | 30 ± 2 | 1 | 88.8 |

TABLE 7(e)

| Period of Time (hours) | Reaction Temperature (° C) | Reaction Pressure (PSIG) | Exit Stream Flowrate (lbs./hr.) | Weight % 2-chloroethyl- phosphonic acid in reaction product |
|---|---|---|---|---|
| 5 | 150 | 0 | 3 | 37.8 |
| 10 | 150 | 0 | 3 | 53.2 |
| 15 | 150 | 0 | 3 | 64.4 |
| 20 | 150 | 0 | 3 | 72.7 |
| 25 | 150 | 0 | 3 | 77.0 |
| 30 | 150 | 0 | 3 | 80.6 |
| 43 | 150 | 30 ± 2 | 1 | 87.8 | decrease somewhat of the rate of conversion into 2-chloroethylphosphonic acid.

TABLE 9(a)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 160 | 15 ± 2 | 3 | 49.9 |
| 10 | 160 | 15 ± 2 | 3 | 62.1 |
| 15 | 160 | 15 ± 2 | 3 | 74.6 |
| 20 | 160 | 15 ± 2 | 3 | 81.7 |
| 25 | 160 | 15 ± 2 | 3 | 84.8 |

TABLE 9(b)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 160 | 30 ± 2 | 3 | 44.4 |
| 10 | 160 | 30 ± 2 | 3 | 52.0 |
| 15 | 160 | 30 ± 2 | 3 | 63.6 |
| 20 | 160 | 30 ± 2 | 3 | 68.9 |
| 25 | 160 | 30 ± 2 | 3 | 79.8 |

EXAMPLE X

COMPARATIVE EXAMPLE

This Example clearly indicates that during at least the first 25 hours of reaction time i.e. the first period of time, the higher the exit stream flowrate the greater the rate of conversion to 2-chloroethylphosphonic acid; and that increasing the pressure during this period of time decreases somewhat the rate of conversion to 2-chloroethylphosphonic acid.

TABLE 10(a)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 0 | 0.5 | 20.8 |
| 10 | 150 | 0 | 0.5 | 27.8 |
| 15 | 150 | 0 | 0.5 | 35.6 |
| 20 | 150 | 0 | 0.5 | 39.4 |
| 25 | 150 | 0 | 0.5 | 43.9 |
| 30 | 150 | 0 | 0.5 | 47.5 |
| 35 | 150 | 0 | 0.5 | 55.1 |

TABLE 10(b)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 0 | 1 | 28.6 |
| 10 | 150 | 0 | 1 | 35.6 |
| 15 | 150 | 0 | 1 | 44.8 |
| 20 | 150 | 0 | 1 | 51.9 |
| 25 | 150 | 0 | 1 | 55.5 |
| 30 | 150 | 0 | 1 | 63.8 |
| 35 | 150 | 0 | 1 | 68.2 |

TABLE 10(c)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 5 - 10 | 0.5 | 26.8 |
| 10 | 150 | 5 - 10 | 0.5 | 30.1 |
| 15 | 150 | 5 - 10 | 0.5 | 35.0 |
| 20 | 150 | 5 - 10 | 0.5 | 38.5 |
| 25 | 150 | 5 - 10 | 0.5 | 41.5 |
| 29 | 150 | 5 - 10 | 0.5 | 43.5 |

TABLE 10(d)

| Period of Time (hours) | Reaction Temp. (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 15 ± 2 | 1 | 27.5 |
| 10 | 150 | 15 ± 2 | 1 | 34.2 |
| 15 | 150 | 15 ± 2 | 1 | 35.0 |
| 20 | 150 | 15 ± 2 | 1 | 43.2 |
| 25 | 150 | 15 ± 2 | 1 | 44.9 |

TABLE 10(e)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 15 ± 2 | 2 | 40.7 |
| 10 | 150 | 15 ± 2 | 2 | 46.1 |
| 15 | 150 | 15 ± 2 | 2 | 51.2 |
| 20 | 150 | 15 ± 2 | 2 | 55.3 |
| 25 | 150 | 15 ± 2 | 2 | 63.2 |

TABLE 10(f)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 15 ± 2 | 3 | 37.3 |
| 10 | 150 | 15 ± 2 | 3 | 49.4 |
| 15 | 150 | 15 ± 2 | 3 | 61.4 |
| 20 | 150 | 15 ± 2 | 3 | 72.7 |
| 25 | 150 | 15 ± 2 | 3 | 79.6 |

TABLE 10(g)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 30 ± 2 | 1 | 33.4 |
| 10 | 150 | 30 ± 2 | 1 | 42.0 |
| 15 | 150 | 30 ± 2 | 1 | 41.6 |
| 20 | 150 | 30 ± 2 | 1 | 47.5 |
| 25 | 150 | 30 ± 2 | 1 | 51.0 |

TABLE 10(h)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 30 ± 2 | 2 | 31.1 |
| 10 | 150 | 30 ± 2 | 2 | 39.2 |
| 15 | 150 | 30 ± 2 | 2 | 46.7 |
| 20 | 150 | 30 ± 2 | 2 | 54.1 |
| 25 | 150 | 30 ± 2 | 2 | 60.0 |

TABLE 10(i)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5 | 150 | 30 ± 2 | 3 | 37.6 |
| 10 | 150 | 30 ± 2 | 3 | 50.2 |
| 15 | 150 | 30 ± 2 | 3 | 56.8 |
| 20 | 150 | 30 ± 2 | 3 | 67.0 |
| 28 | 150 | 30 ± 2 | 3 | 75.6 |

What is claimed:

1. In a process for the manufacture of an aliphatic phosphonic acid of the formula:

TABLE 7(f)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 150 | 0      | 3 | 39.7 |
| 10 | 150 | 0      | 3 | 54.3 |
| 15 | 150 | 0      | 3 | 65.4 |
| 20 | 150 | 0      | 3 | 72.2 |
| 25 | 150 | 0      | 3 | 75.1 |
| 30 | 150 | 0      | 3 | 79.3 |
| 43 | 150 | 30 ± 2 | 1 | 89.0 |

TABLE 7(g)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 150 | 0      | 3 | 38.2 |
| 10 | 150 | 0      | 3 | 57.3 |
| 15 | 150 | 0      | 3 | 67.0 |
| 20 | 150 | 0      | 3 | 74.1 |
| 25 | 150 | 0      | 3 | 77.7 |
| 30 | 150 | 0      | 3 | 80.1 |
| 43 | 150 | 30 ± 2 | 1 | 88.8 |

TABLE 7(h)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 150 | 0      | 3 | 42.2 |
| 10 | 150 | 0      | 3 | 52.5 |
| 15 | 150 | 0      | 3 | 65.6 |
| 20 | 150 | 0      | 3 | 71.8 |
| 25 | 150 | 0      | 3 | 76.5 |
| 30 | 150 | 0      | 3 | 79.6 |
| 35 | 150 | 30 ± 2 | 1 | 85.9 |
| 42 | 150 | 30 ± 2 | 1 | 88.0 |

TABLE 7(i)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 150 | 0      | 3 | 40.7 |
| 10 | 150 | 0      | 3 | 54.0 |
| 15 | 150 | 0      | 3 | 63.6 |
| 20 | 150 | 0      | 3 | 71.5 |
| 25 | 150 | 0      | 3 | 75.4 |
| 30 | 150 | 30 ± 2 | 0 | 83.3 |
| 35 | 150 | 30 ± 2 | 0 | 84.7 |
| 40 | 150 | 30 ± 2 | 0 | 84.8 |

TABLE 7(j)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 150 | 2       | 5   | 48.7 |
| 10 | 150 | 2       | 5   | 63.0 |
| 15 | 150 | 2       | 5   | 72.5 |
| 20 | 150 | 15 – 20 | 0.5 | 77.6 |
| 28 | 150 | 15 – 20 | 0.5 | 80.1 |

TABLE 7(k)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 150 | 5 – 10 | 2 | 37.3 |
| 10 | 150 | 5 – 10 | 2 | 44.5 |
| 15 | 150 | 5 – 10 | 2 | 57.6 |
| 20 | 150 | 5 – 10 | 2 | 66.0 |
| 25 | 150 | 5 – 10 | 2 | 75.3 |
| 30 | 150 | 5 – 10 | 2 | 80.7 |
| 38 | 150 | 5 – 10 (2 hrs.) 15 – 20 (6 hrs.) | 2 (2 hrs.) 1 (6 hrs.) | 85.8 |

EXAMPLE VIII

This Example indicates the process of this invention utilized at 160° C.

TABLE 8(a)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 160 | 0      | 2 | 38.8 |
| 10 | 160 | 0      | 2 | 50.5 |
| 15 | 160 | 0      | 2 | 55.0 |
| 20 | 160 | 0      | 2 | 73.9 |
| 25 | 160 | 0      | 2 | 77.8 |
| 30 | 160 | 0      | 2 | 80.6 |
| 36 | 160 | 30 ± 2 | 2 | 86.4 |
| 43 | 160 | 30 ± 2 | 2 | 88.5 |

TABLE 8(b)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 160 | 0      | 3 | 44.4 |
| 10 | 160 | 0      | 3 | 60.4 |
| 15 | 160 | 0      | 3 | 70.4 |
| 20 | 160 | 0      | 3 | 76.1 |
| 25 | 160 | 0      | 3 | 79.9 |
| 30 | 160 | 0      | 3 | 82.0 |
| 36 | 160 | 30 ± 2 | 1 | 87.7 |
| 43 | 160 | 30 ± 2 | 1 | 88.7 |

TABLE 8(c)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 160 | 15 ± 2 | 3 | 49.1 |
| 10 | 160 | 15 ± 2 | 3 | 61.7 |
| 15 | 160 | 15 ± 2 | 3 | 73.9 |
| 20 | 160 | 15 ± 2 | 3 | 79.9 |
| 25 | 160 | 30 ± 2 | 1 | 85.0 |
| 35 | 160 | 30 ± 2 | 1 | 86.7 |
| 40 | 160 | 30 ± 2 | 1 | 87.6 |
| 43 | 160 | 30 ± 2 | 1 | 87.5 |

TABLE 8(d)

| Period of Time (hours) | Reaction Temperature (° C) | Reaction Pressure (PSIG) | Exit Stream Flowrate (lbs./hr.) | Weight % 2-chloroethyl-phosphonic acid in reaction product |
|---|---|---|---|---|
| 5  | 160 | 15 ± 2 | 3 | 45.5 |
| 10 | 160 | 15 ± 2 | 3 | 60.5 |
| 15 | 160 | 15 ± 2 | 3 | 73.2 |
| 20 | 160 | 15 ± 2 | 3 | 80.8 |
| 25 | 150 | 15 ± 2 | 1 | 84.2 |
| 30 | 150 | 30 ± 2 | 1 | 86.2 |
| 35 | 150 | 30 ± 2 | 1 | 86.8 |
| 40 | 150 | 30 ± 2 | 1 | 87.0 |
| 43 | 150 | 30 ± 2 | 1 | 86.9 |

EXAMPLE IX

COMPARATIVE EXAMPLE

This Example shows tests performed at a temperature of 160° C. From this comparative Example it can be seen that an increase in pressure during the first 25 hours of reaction time, first period of time, results in a of the type wherein a diester of the aliphatic phosphonic acid of the general formula:

is reacted with anhydrous hydrogen halide selected from the group consisting of hydrogen chloride, hydrogen bromide, hydrogen iodide and hydrogen fluoride to produce a reaction product containing the corresponding aliphatic phosphonic acid and the corresponding aliphatic halides,
wherein $R_1$, $R_2$ and $R_3$ are each independently selected from the group consisting of substituted and unsubstituted aryl, alkyl, alkenyl, halo-substituted alkyl and halosubstituted alkenyl, having from 1 to 6 carbon atoms, wherein the improvement comprises
a. reacting the diester and the anhydrous hydrogen halide at a first temperature of at least 100° C, at a low pressure and for a first period of time to form a first reaction product;
b. subsequently reacting the first reaction product and the anhydrous hydrogen halide at a second temperature of at least 100° C, at a high pressure, said high pressure higher than said low pressure, and for a second period of time to form a second reaction product; and
c. removing the aliphatic halides from at least one reaction product.

2. The process of claim 1, wherein the step of removing aliphatic halides is continuous and the aliphatic halides are removed from the first and second reaction products.

3. The process of claim 1, wherein $R_1$, $R_2$ and $R_3$ are the same.

4. The process of claim 1, wherein $R_1$, $R_2$ and $R_3$ are the same halo-substituted alkyl.

5. The process of claim 1, wherein the aliphatic phosphonic acid is 2-chloroethylphosphonic acid.

6. The process of claim 5, wherein the diester is bis(2-chloroethyl)-2-chloroethyl phosphonate.

7. The process of claim 1, wherein the anhydrous hydrogen halide is anhydrous hydrogen chloride.

8. The process of claim 7, wherein the aliphatic halides are ethylene dichloride.

9. The process of claim 1, wherein
a. the aliphatic phosphonic acid is 2-chloroethylphosphonic acid;
b. the diester is bis(2-chloroethyl)-2-chloroethyl phosphonate;
c. the anhydrous hydrogen halide is anhydrous hydrogen chloride; and
d. the aliphatic halides are ethylene dichloride.

10. The process of claim 9, wherein the first and second temperatures are from about 140° C to about 160° C.

11. The process of claim 9, wherein the first and second temperature are no greater than about 200° C.

12. The process of claim 9, wherein the step of removing ethylene dichloride is continuous and the ethylene dichloride is removed from the first and second reaction products; and wherein the steps of: (a) reacting the diester of the anhydrous hydrogen chloride, (b) reacting the first reaction product and the anhydrous hydrogen chloride, and (c) removing aliphatic halides, is accomplished by
i. introducing continuously into the first and second reaction products an entrance stream comprised of anhydrous hydrogen chloride; and
ii. removing continuously from the first and second reaction products an exit stream comprised of unreacted anhydrous hydrogen chloride and ethylene dichloride.

13. The process of claim 12, wherein the unreacted anhydrous hydrogen chloride is separated from the exit stream and introduced into the entrance stream.

14. The process of claim 9, wherein the low pressure is at least about 14 psia and the high pressure is at least about 30 psia.

15. The process of claim 9, wherein the low pressure is from about 14 psia to about 30 psia, and the high pressure is from about 30 psia to about 50 psia.

16. The process of claim 9, wherein the first period of time is until the first reaction product contains at least about 70% by weight of 2-chloroethylphosphonic acid.

17. The process of claim 9, wherein the first period of time is at least about 25 hours.

18. The process of claim 9, wherein the first period of time is from about 25 to about 35 hours.

19. The process of claim 9, wherein the second period of time until the second reaction product contains a required concentration of at least about 80% by weight of 2-chloroethylphosphonic acid.

20. The process of claim 9, wherein the second period of time is at least about 10 hours.

21. The process of claim 9, wherein the second period of time is from about 10 hours to about 16 hours.

22. The process of claim 12, wherein the exit stream flowrate during the first period of time is greater than the exit stream flowrate during the second period of time.

23. The process of claim 22, wherein the weight ratio of the exit stream flowrates is about (3 to 6): 1.

24. In a process for the manufacture of 2-chloroethylphosphonic acid of the type wherein bis(2-chloroethyl)-2-chloroethyl phosphonate is reacted with anhydrous hydrogen chloride to produce a reaction product containing 2-chloroethylphosphonic acid and ethylene dichloride, wherein the improvement comprises:
a. reacting bis(2-chloroethyl)-2-chloroethyl phosphonate and anhydrous hydrogen chloride at a first temperature of at least 100° C, at a low pressure of at least about 14 psia for a first period of time to form a first reaction product, said first period of time is until the first reaction product contains at least about 70% by weight of 2-chloroethylphosphonic acid;
b. subsequently reacting the first reaction product and the anhydrous hydrogen chloride at a second temperature of at least 100° C, at a high pressure of at least about 30 psia, said high pressure higher than said low pressure, and for a second period of time to form a second reaction product, said second period of time is until the second reaction product contains a required concentration of at least about 80% by weight of 2-chloroethylphosphonic acid;
c. continuously removing ethylene dichloride from the first and second reaction product,
wherein the steps of (a) reacting bis(2-chloroethyl)-2-chloroethylphosphonate and anhydrous hydrogen chloride, (b) reacting the first reaction product and anhydrous hydrogen chloride, and (c) removing ethylene dichloride are accomplished by:
  i. introducing continuously into the first and second reaction products an entrance stream comprised of anhydrous hydrogen chloride; and
  ii. removing continuously from the first and second reaction products an exit stream comprised of unreacted anhydrous hydrogen chloride and ethylene dichloride.

25. The process of claim 24, wherein the unreacted anhydrous hydrogen chloride is separated from the exit stream and introduced into the entrance stream.

26. The procss of claim 24, wherein the first and second temperatures are from about 140° C to about 160° C.

27. The process of claim 24, wherein the first and second temperatures are no greater than about 200° C.

28. The process of claim 24, wherein the low pressure is from about 14 psia to about 30 psia.

29. The process of claim 24, wherein the high pressure is from about 30 psia to about 50 psia.

30. The process of claim 24, wherein the first period of time is at least 25 hours.

31. The process of claim 24, wherein the first period of time is from about 25 to about 35 hours.

32. The process of claim 24, wherein the second period of time is at least 10 hours.

33. The process of claim 24, wherein the second period of time is from about 10 hours to about 16 hours.

34. The process of claim 24, wherein the exit stream flowrate during the first period of time is greater than the exit stream flowrate during the second period of time.

35. The process of claim 34, wherein the weight ratio of the exit stream flowrate is about (3 to 6) : 1.

* * * * *

UNITED STATES PATENT OFFICE
CERTIFICATE OF CORRECTION

Patent No. 4,064,163          Dated December 20, 1977

Inventor(s) John E. Drach et al.

It is certified that error appears in the above-identified patent and that said Letters Patent are hereby corrected as shown below:

Column 1, line 22, "b" should be omitted.

Column 3, line 34 "STEP II" should read "STEP III".

Column 10, line 37 "liner" should read "linear".

Column 13, line 38, after "concentration of" insert --2-chloroethylphosphonic acid continually increases and the concentration of the --.

Column 14, line 32 after "reaction" insert --rate is increased. In Equation (1) an increase--.

Column 15, line 64, "th" should read "the".

UNITED STATES PATENT OFFICE
CERTIFICATE OF CORRECTION

Patent No. 4,064,163　　　　　　　　Dated December 20, 1977

Inventor(s) John E. Drach et al.

It is certified that error appears in the above-identified patent and that said Letters Patent are hereby corrected as shown below:

(CONTINUED)

Column 22, Table 8(c) between lines 41 and 42 insert the following:

| Period of Time (hours) | Reaction Temperature (°C) | Reaction Pressure (PSIG) | Exit Stream Flowrate (lbs./hr.) | Weight % 2-chloroethyl-phosphonic acid in reaction product |
|---|---|---|---|---|
| 30 | 160 | 30 ± 2 | 1 | 87.0 |

Signed and Sealed this

Twentieth Day of June 1978

[SEAL]

Attest:

RUTH C. MASON
Attesting Officer

DONALD W. BANNER
Commissioner of Patents and Trademarks